United States Patent
Marshall et al.

(10) Patent No.: US 8,110,797 B2
(45) Date of Patent: Feb. 7, 2012

(54) ELECTROSPRAY IONIZATION MASS SPECTROMETRY METHODOLOGY

(75) Inventors: Alan G. Marshall, Tallahassee, FL (US); Priyanka Juyal, Tallahassee, FL (US); Ryan P. Rodgers, Tallahassee, FL (US)

(73) Assignee: Florida State University Research Foundation, Inc., West Palm Beach, FL (US)

( * ) Notice: Subject to any disclaimer, the term of this patent is extended or adjusted under 35 U.S.C. 154(b) by 171 days.

(21) Appl. No.: 12/700,992

(22) Filed: Feb. 5, 2010

(65) Prior Publication Data
US 2010/0230587 A1    Sep. 16, 2010

Related U.S. Application Data

(60) Provisional application No. 61/150,537, filed on Feb. 6, 2009.

(51) Int. Cl.
*B01D 59/44*    (2006.01)
*H01J 49/26*    (2006.01)

(52) U.S. Cl. .................... 250/288; 250/423 R; 250/424; 250/425

(58) Field of Classification Search ........... 250/281.281, 250/288, 423 R, 424, 42
See application file for complete search history.

(56) References Cited

U.S. PATENT DOCUMENTS

| | | | | |
|---|---|---|---|---|
| 5,523,566 | A * | 6/1996 | Fuerstenau et al. | 250/282 |
| 6,288,390 | B1 * | 9/2001 | Siuzdak et al. | 250/288 |
| 6,512,060 | B1 * | 1/2003 | Matyjaszewski et al. | 526/111 |
| 6,541,580 | B1 * | 4/2003 | Matyjaszewski et al. | 526/90 |
| 7,125,938 | B2 * | 10/2006 | Matyjaszewski et al. | 526/147 |
| 7,678,869 | B2 * | 3/2010 | Matyjaszewski et al. | 526/130 |
| 7,888,127 | B2 * | 2/2011 | Becker | 436/94 |
| 2002/0043651 | A1 * | 4/2002 | Darrow et al. | 252/408.1 |
| 2011/0172124 | A1 * | 7/2011 | Becker | 506/17 |

* cited by examiner

*Primary Examiner* — Bernard E Souw
(74) *Attorney, Agent, or Firm* — Novak Druce + Quigg LLP (57) ABSTRACT

A method of enhanced speciation of both positive and negatives species in an analyte is disclosed. The method can include producing a first analyte solution comprising an analyte composition and an effective amount of silver triflate, and analyzing the first analyte solution with an electrospray ionization mass spectrometer. The method can also include producing a second analyte solution comprising a portion of the analyte composition and an effective amount of a compound of formula I, and analyzing the second analyte solution with an electrospray ionization mass spectrometer. The compound of formula I is [NX$^+$][OH$^-$], where X is a linear, branched, or cyclic $C_1$-$C_{10}$ alkane; an aryl; a heterocyclic aromatic; or a heterocyclic moiety.

20 Claims, 12 Drawing Sheets

ELECTROSPRAY IONIZATION MASS SPECTROMETRY METHODOLOGY

CROSS-REFERENCE TO RELATED APPLICATIONS

This application claims priority to U.S. Provisional Application No. 61/150,537 filed Feb. 6, 2009, entitled "Electrospray Ionization Mass Spectrometry Methodology," the entirety of which is incorporated by reference herein.

STATEMENT REGARDING FEDERALLY SPONSORED RESEARCH OR DEVELOPMENT

The United States Government has rights in this invention pursuant to contract no. DMR 0654118 between the National Science foundation and Florida State University.

FIELD OF THE INVENTION

The invention relates to a method of enhanced electrospray ionization mass spectroscopy.

BACKGROUND

With global increases in consumption of the easily available resources of crude oil, the petroleum industry has moved toward alternative sources, such as extra heavy oils from less accessible areas, e.g., deepwater production, and processing intensive oil resources such as the bitumen. However, the production, transportation and refining of these resources presents many problems and challenges for the oil industry. In order to fully utilize these alternative materials, compositional knowledge must be developed in order to efficiently generate energy and tailor feasible solutions to overcome the problems associated with refining and utilization of these petroleum resources. From health, safety and environmental perspectives, air pollution caused by emissions of $SO_X$ and $NO_X$, and soot or other particulate matter from the combustion of petroleum fuels is a matter of significant concern. Intensive research and development efforts to develop better catalysts, processes and solutions for rigorous refining operations are paramount in order to limit the amount of sulfur, nitrogen and aromatic waste, and produce ultra-clean transportation fuels that meet existing fuel regulations. The chemical structure of different petroleum heteroatom (S, N, and O) containing molecules determines their behavior in production and upgrading. Therefore, efficient and economic exploitation of these new energy resources hinges on the detailed understanding of the chemistry and structure of the constituents of these complex natural resources.

Advances in FT-ICR MS have made it possible to achieve high resolving power and mass accuracy in order to resolve and provide detailed compositional information for complex mass spectra of some analytes, such as crude oil and bitumen. Electrospray ionization Fourier transform ion cyclotron resonance mass spectrometry (ESI FT-ICR MS) has the potential to provide critical information on the polar compound inventories of crude oils. However, the chemical scope of ESI mass spectrometry is limited by analyte acidity or basicity in common ESI solvent systems (toluene and methanol) and are unable to provide complete compositional analysis of many neutral or near-neutral compounds in a complex matrix, such as crude oil or bitumen.

SUMMARY OF THE INVENTION

In one embodiment, the invention is drawn to an electrospray ionization mass spectrometry methodology. The method can include obtaining an analyte solution comprising an analyte composition and an effective amount of a compound of formula I, and analyzing the analyte solution with an electrospray ionization mass spectrometer. The compound of formula I can be:

where X is a linear, branched, or cyclic $C_1$-$C_{10}$ alkane; an aryl; a heterocyclic aromatic; or a heterocyclic moiety. The four X ligands can be the same or different.

The analyte composition can include a petroleum compound. The analyte composition can include crude oil, bitumen, a fraction thereof, a concentrate thereof, or a component thereof.

The compound of formula I can be tetrabutylammonium hydroxide or tetramethyl ammonium hydroxide. The mass ratio of analyte composition to compound of Formula I can range from 10,000:1 to 1:3.

The analyzing step comprises analyzing said analyte solution with said electrospray ionization mass spectrometer in negative ion mode.

The method is also drawn to an electrospray ionization mass spectrometry methodology that includes obtaining an analyte solution comprising an analyte composition and an effective amount of silver triflate, and analyzing said analyte solution with an electrospray ionization mass spectrometer. The analyzing step can include analyzing the analyte solution with the electrospray ionization mass spectrometer in positive ion mode. The mass ratio of analyte composition to silver triflate can range from 3:1 to 1:10.

These and other embodiments are described in more detail below.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

A method for enhanced speciation of an analyte composition using electrospray ionization mass spectrometry (ESI-MS). Using conventional ESI-MS techniques, solution phase acidity and basicity largely determine the mass spectral response of the analyte. Highly acidic species have a much larger response than weakly acidic species, regardless of their concentration in the sample. The method and ionization agents described herein provide substantially improved speciation of compounds in a hydrocarbon-rich analyte composition, such as crude oil, bitumen, fractions thereof, concentrates thereof, extracts thereof, dilutes thereof, components thereof, and mixtures containing the same.

In one embodiment, the method of enhanced speciation of an analyte composition can involve producing a first analyte solution including an analyte composition and an effective amount of silver triflate. A second analyte solution can be produced that includes a portion of the analyte composition and an effective amount of a compound of Formula I. The first analyte solution and second analyte solution can be separately analyzed using an electrospray ionization mass spectrometer.

The compound of Formula I can have the form:

[NX$_4^+$][OH$^-$]

As used in Formula I, X can be a linear, branched, or cyclic $C_1$-$C_{10}$ alkane; an aryl; a heterocyclic aromatic; or a heterocyclic moiety. The compound of Formula I can be tetrabutylammonium hydroxide or tetramethyl ammonium hydroxide. In other variations, X can be a linear, branched, or cyclic $C_1$-$C_5$ alkane or an aryl. Aryl compounds include, but are not limited to phenyl, benzyl, tolyl, xylyl, thiophene and indolyl. Each of the four X ligands can be the same or different.

The analyte composition can include a nonpolar compound, a petroleum compound, or both. The analyte composition can include crude oil, bitumen, a fraction thereof, a concentrate thereof, a dilute thereof, a component thereof, or a mixture containing the same.

Analysis of the first analyte solution can include analyzing the first analyte solution with an electrospray ionization mass spectrometer in positive ion mode. Analysis of the second analyte solution can include analyzing the second analyte solution with the electrospray ionization mass spectrometer in negative ion mode. The electrospray ionization mass spectrometer can be an electrospray ionization Fourier transform ion cyclotron resonance mass spectrometer (ESI FT-ICR MS).

The amount of the ionization reagents, e.g., silver triflate and compound of Formula I, added to the analyte can be an effective amount. As used herein, an "effective amount" is an amount sufficient to produce speciation of the analyte that is superior to that of previous techniques, e.g., formic acid and ammonium hydroxide, respectively. In particular, superior speciation of $N_1$, $N_1O_1$, $N_1S_1$, HC, $S_1$ and/or $S_2$ in negative ion mode and speciation of $S_1$, $S_2$, $S_3$, HC, OS, NS in positive ion mode.

Although the exact amount of the ionization reagents can vary depending on the specific analyte solution, the ionization reagent, and the desired measurement, the mass ratio of analyte composition to compound of Formula I can range from 10,000:1 to 1:3. The mass ratio of analyte composition to compound of Formula I can range from 100:1 and 10:1, or even from 1:1 to 5:1. Similarly, the mass ratio of analyte composition to silver triflate can be 3:1 to 1:10. The mass ratio of analyte to silver triflate can be between 1:1 and 1:3 or between 4:1 and 1:1.

The method can include a reaction of the ionization agents with the target species in the analyte composition for a sufficient time to convert the target species into an ionic target species. As the ionization reagents, silver triflate and compounds of Formula I, are highly reactive even when the target species are neutral, the reacting step can occur as direct capillary mixing just prior to ionization in the ESI. The duration of the reacting step can be at least 1 second, at least 5 seconds, at least 15 seconds, or at least 30 seconds.

In positive ion mode, silver triflate is used as an ionization reagent that has a strong ability to bind to a source of electrons, e.g., electrons in n, π or σ orbitals, and offers a rapid method that highlights the basic crude oil matrix by generating positively charged complexes of silver ions with crude oil components. In negative ion mode, compounds of Formula I are used due to their oil solubility and pronounced basic strength which enables ESI-MS to detect near-neutral molecules as negative ions. In both instances, use of the extremely active ionization reagents enables enhanced identification of hydrocarbon and heteroatom-containing hydrocarbon species in complex mixtures containing hydrocarbons, such as crude oil, bitumen, fractions thereof, concentrates thereof, components thereof, and mixtures containing the same.

EXAMPLE 1

Sample Preparation

Positive ion ESI FT-ICR MS: One part of crude oil (1 mg/mL in 1:1 (v/v) toluene:methanol) was mixed with 3 parts of silver triflate and vortexed just before injection into the ESI source. The result was compared to crude oil (1 mg/mL in 1:1 (v/v) toluene:methanol) mixed with 1% by volume formic acid.

Negative ion ESI FT-ICR MS: All crude oil samples were dissolved in a 2:1 (v/v) solution of toluene/methanol at a concentration of 1 mg/mL. Three different ionization reagent solutions were prepared: (1) 25 wt-% tetramethyl ammonium hydroxide (TMAH) in methanol ("organic TMAH"), (2) 25 wt-% TMAH in water ("aqueous TMAH"), and (3) 28 wt-% ammonia in water ("ammonium hydroxide"). Each of the three ionization reagent solutions were spiked into the crude oil solution at a volume ratio of 10 μL per mL of analyte solution. The reagents and sample solutions were vortexed for a few seconds before being injected into the ESI source.

All reagents and solvents used in these analytical evaluations were the highest purity grade available from Fisher-Scientific and Sigma-Aldrich Analytical Instrumentation and Techniques: The samples were analyzed using a custom built ESI FT-ICR mass spectrometer system capable of producing a 9.4 T magnetic field that was equipped with a PREDATOR data station. Calibration of the instrument was achieved with Agilent (Palo Alto, Calif.) HP mix. Singly charged ions with a relative abundance greater than six times the standard deviation of the baseline noise were Kendrick-sorted and imported into Microsoft Excel for identification with a formula calculator. The mass tolerance was set to ±1 ppm and Kendrick mass defect was used to identify homologous series and peak assignments.

Results and Discussion

Positive Ion Mode ESI FT-ICR MS

Silver triflate was used as the ionization reagent for positive ion mode ESI FT-ICR. MS. The triflate or trifluoromethanesulfonate anion, $CF_3SO_3^-$, is resonance stabilized due to the dispersal of negative charge over three oxygen atoms and the sulfur atom. An additional stabilization is achieved by the strong electron-withdrawing effect of the trifluoromethyl group, which causes the triflate anion to be among the fastest leaving groups, i.e., most rapid dissociation and stability in the anion form. Based on the following results, it is believed that the exemplary stability and non-nucleophilicity of the triflate anion enhances the electron-affinity of the silver cation and thus favors complex formation with both polar and non-polar molecules.

Figure 1:
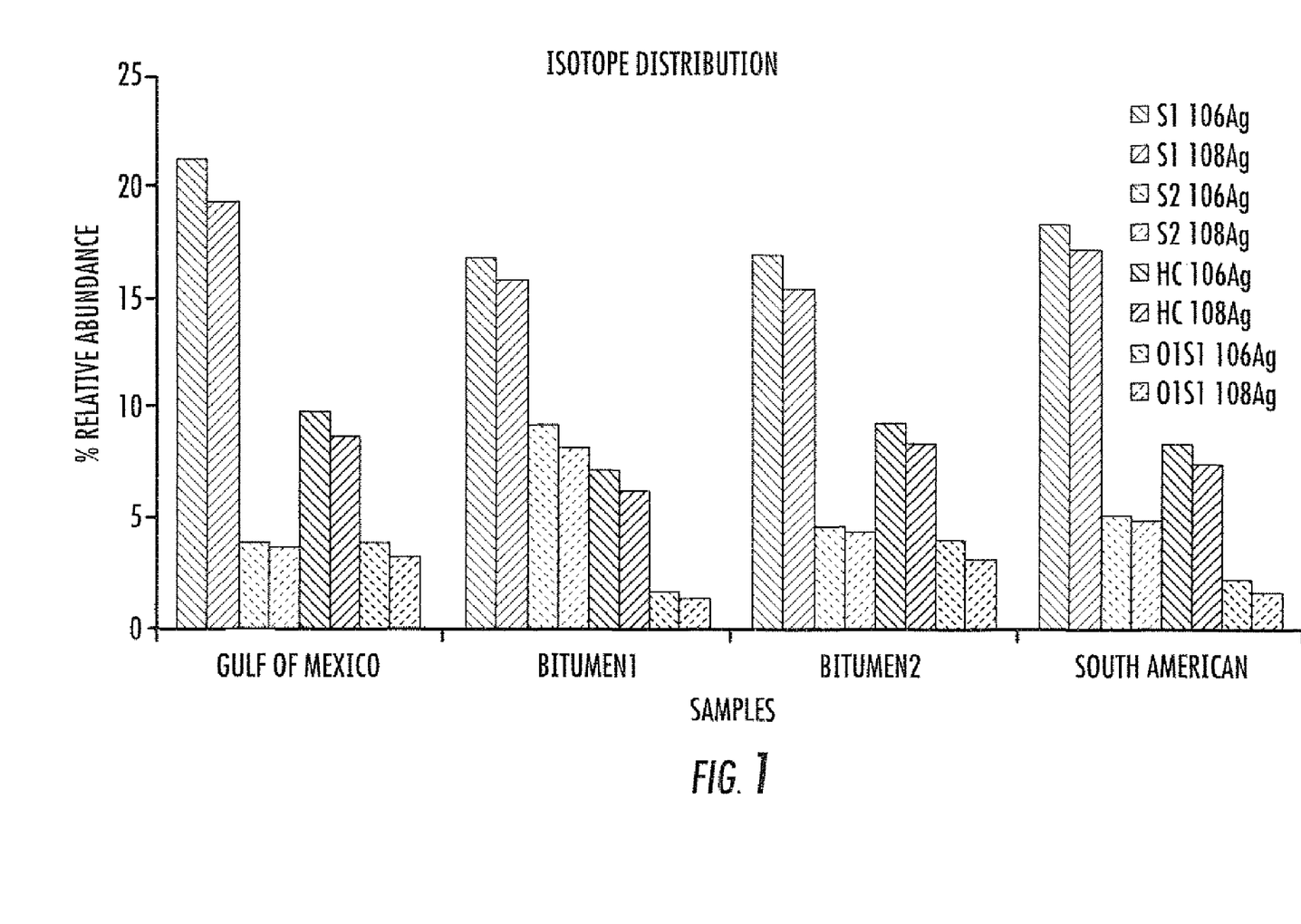
FIG. 1 is a graph of positive ion mode ESI-MS results showing the relative abundance of heteroatom classes for several oil bitumen samples using silver triflate.

FIG. 1 shows the isotopic distribution for $^{106}Ag$ and $^{108}Ag$ for each of the heteroatom classes $S_1$, $S_2$, hydrocarbon ("HC") and OS based on positive ion mode ESI MS for several crude oil and bitumen samples. The distinctive isotope distribution follows the natural relative abundance of the silver isotopes (51.84% $^{106}Ag$ and 48.16% $^{108}Ag$) and allows verification of elemental composition assignments. The excellent nucleophilicity of sulfur, which is much greater than that for oxygen or nitrogen, allows for adduction with electrophilic $Ag^+$ cations. Thus, using silver triflate demonstrates that both polar and non-polar S classes are abundant in crude oil and bitumen. As expected, the nonpolar S classes ($S_1$ and $S_2$) as well as hydrocarbons (HC) are absent in conventional positive ion ESI mass spectra. Thus, the method disclosed herein allows spectroscopic observation of atomic classes that are not observed in conventional positive ESI MS.

Figure 2:
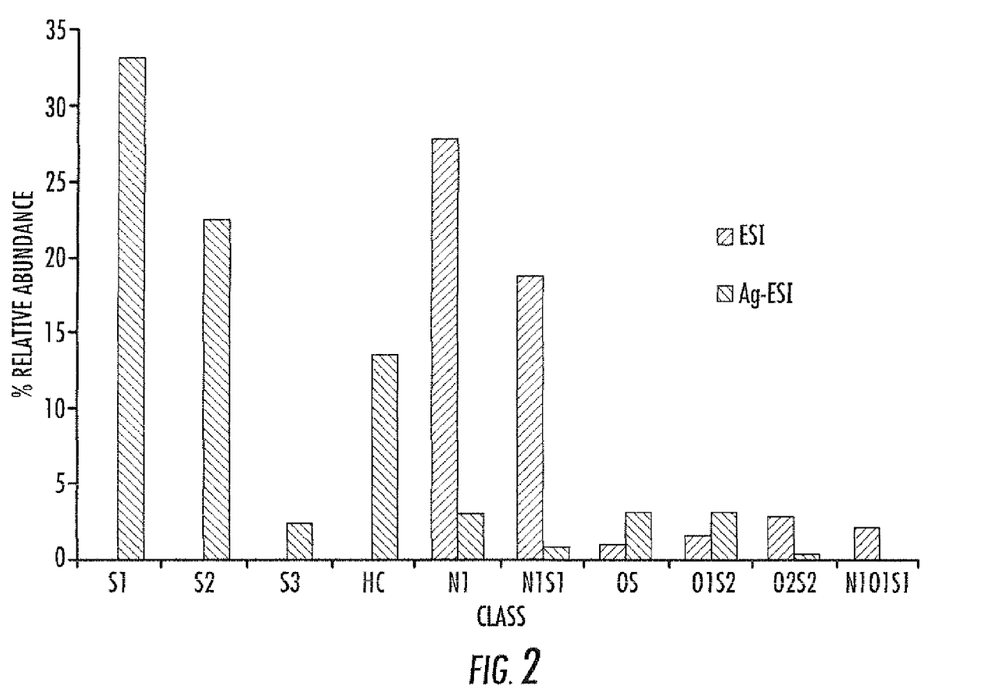
FIG. 2 is a graph of positive ion mode ESI-MS results showing a comparative class distribution of selected heteroatoms for a Canadian bitumen sample using silver triflate and conventional ionizing reagents.
Figure 3A:
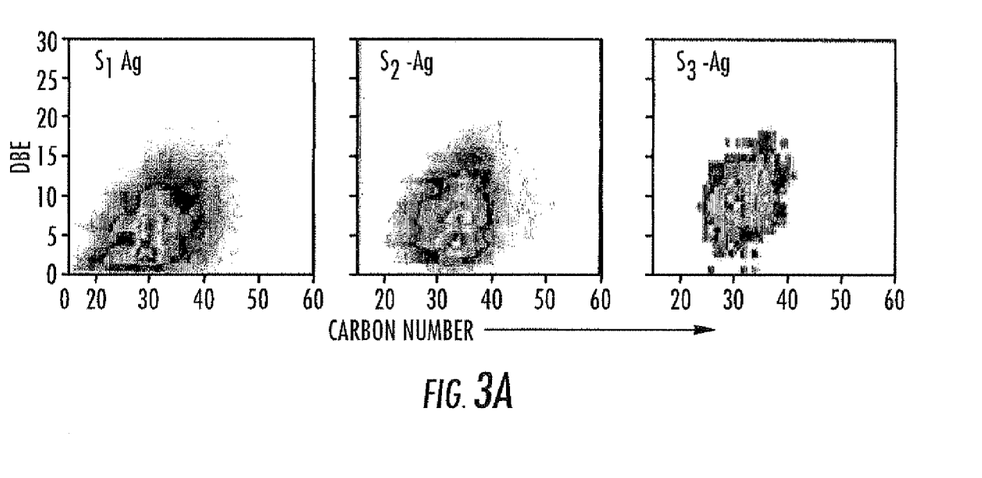
FIG. 3(A) is a series of graphs of positive ion mode ESI FT-ICR MS results showing the isoabundance-contoured DBE versus carbon number images for $S_1$, $S_2$ and $S_3$ classes for a Canadian bitumen sample using silver triflate. No results were obtained using formic acid as the ionization reagent.
Figure 3B:
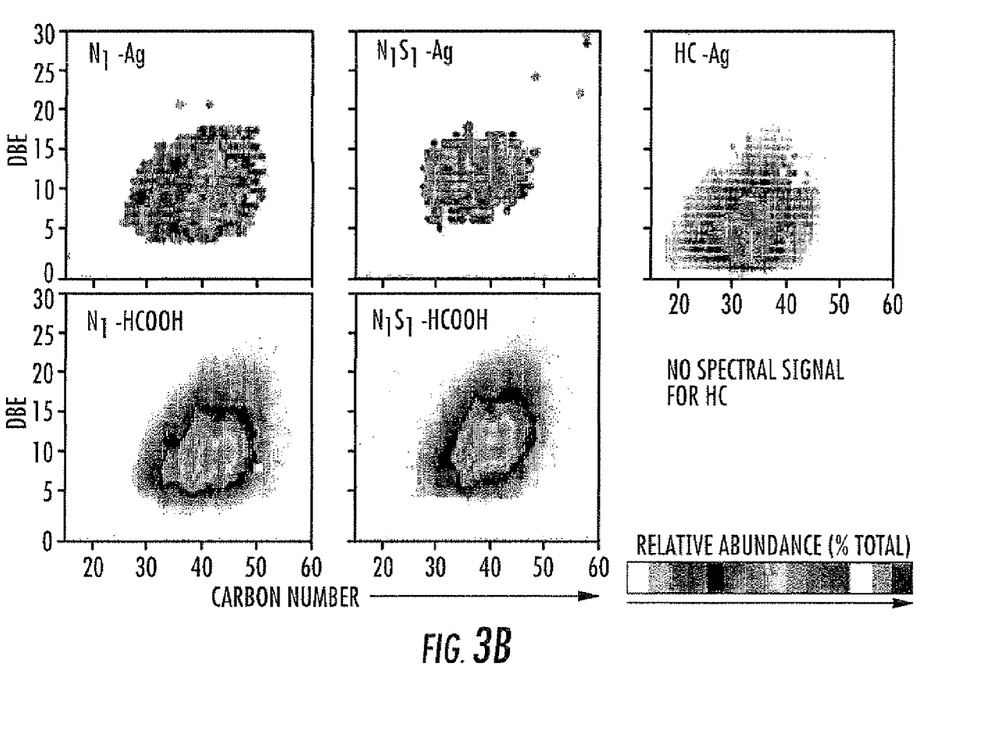
FIG. 3(B) is a series of graphs of positive ion mode ESI FT-ICR MS results showing the isoabundance-contoured DBE versus carbon number images for $N_1$, $N_1S_1$ and hydrocarbon (HC) class for a Canadian bitumen sample using silver triflate and formic acid. No results were obtained or hydrocarbons using formic acid as the ionization reagent.

Sulfur-containing classes included $S_1$, $S_2$, $S_3$, OS, and NS. As seen in FIG. 2 and FIG. 3(B), the $S_1$, $S_2$, and $S_3$ classes were not detected by conventional positive-ion ESI mass spectra of oil samples spiked with formic acid. However, as shown in FIG. 3(B), silver triflate can be used to identify non-polar compound classes, including hydrocarbon classes, for all of the oil samples that are not observable using conventional ESI MS.

Other ionization methods for nonvolatile high-boiling petroleum materials, such as atmospheric pressure photoionization (APPI), field desorption (FD), matrix-assisted laser desorption/ionization (MALDI), and chemical ionization (CI), either have low throughput or involve thermal processes that may cause degradation of the analyte molecules or otherwise limit observation and identification of the analyte molecules. Mix-and-spray silver cation complexation using silver triflate avoids tedious separations and lengthy reaction periods and the need for thermal desorption. Hence, silver adduction overcomes the failure of conventional ESI-MS for rapid speciation of neutral heterocycles, specifically sulfur-heterocycles, and hydrocarbons in complex crude oils without the thermal desorption limitations associated with APPI, APLI and CI.

While it is not necessary to practice the invention and while not wishing to be bound by theory, it is believed that silver triflate ionizes to form $Ag^+$ cations that form complexes with electronegative atoms and the n-electron system of non-polar aromatic hydrocarbons, such as those found in complex crude oils and bitumen. The silver cation is believed to produce adducts with sources of n, π or σ electrons by cation-π interaction, host-guest, or donor-acceptor chemistry. These interactions enable silver triflate to produce mass spectroscopy results with unparalleled resolution, particularly with respect to non-polar species.

Negative Ion Mode ESI FT-ICR MS

Figure 4:
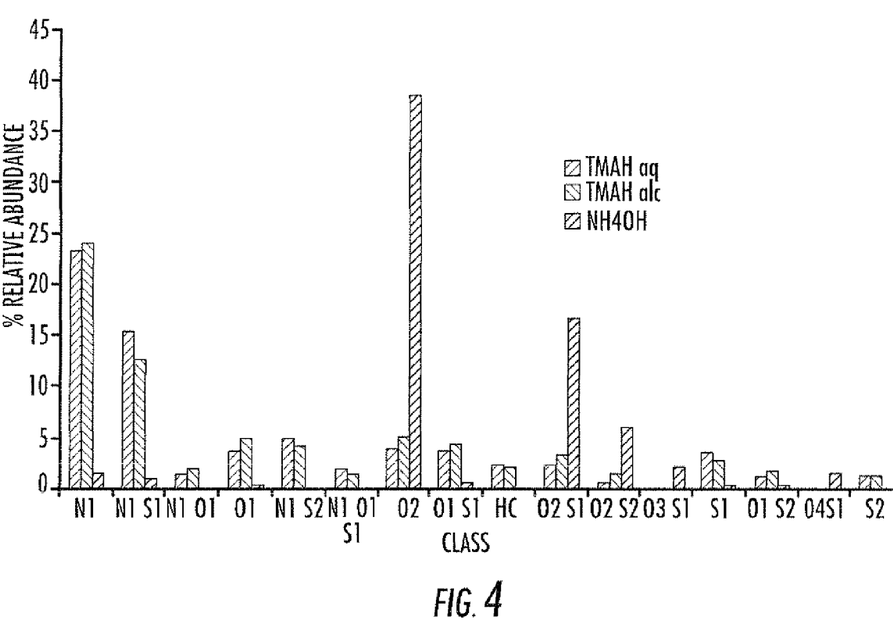
FIG. 4 is a graph showing comparative results of heteroatom class distributions detected using ESI-MS for a Canadian bitumen sample using aqueous TMAH, organic TMAH, and ammonium hydroxide.

Conventional negative ESI MS is often complicated by efficiently ionized carboxylic acid species present in petroleum or complex natural mixtures. However, as shown in FIG. 4, oxygen ($O_2$) is the most abundant class identified by ionization with conventional ammonium hydroxide in all oil samples, while $N_1$ is the most abundant class in the TMAH spiked samples. It is believed that mass spectra generated with ammonium hydroxide display disproportionately large carboxylic acid species relative to other neutral and near-neutral species in crude oil because carboxylic acids are more acidic (lower $pK_a$'s) and more readily deprotonated compared to the pyrrolic nitrogen species (high pKa's). Deprotonation efficiency of neutral compounds is further diminished by the matrix effect resulting from the presence of carboxylic acids. Hence, the TMAH spiked samples demonstrate that ion relative abundances measured using ammonium hydroxide will not correlate to the ion relative abundances of neutral precursors in the original sample. So, even though the $O_2$ class is most abundant for most crude oil and bitumen samples spiked with ammonium hydroxide in negative-ion mode ESI MS, analysis with TMAH demonstrates that the $O_2$ class, e.g., naphthenic acid, is not the most abundant class in the source oil matrix. From this, it can be seen that TMAH effectively levels the ionization efficiently across a broad range of heteroatom classes (chemical functionalities) and provides a more complete inventory of petroleum species.

Figure 5:
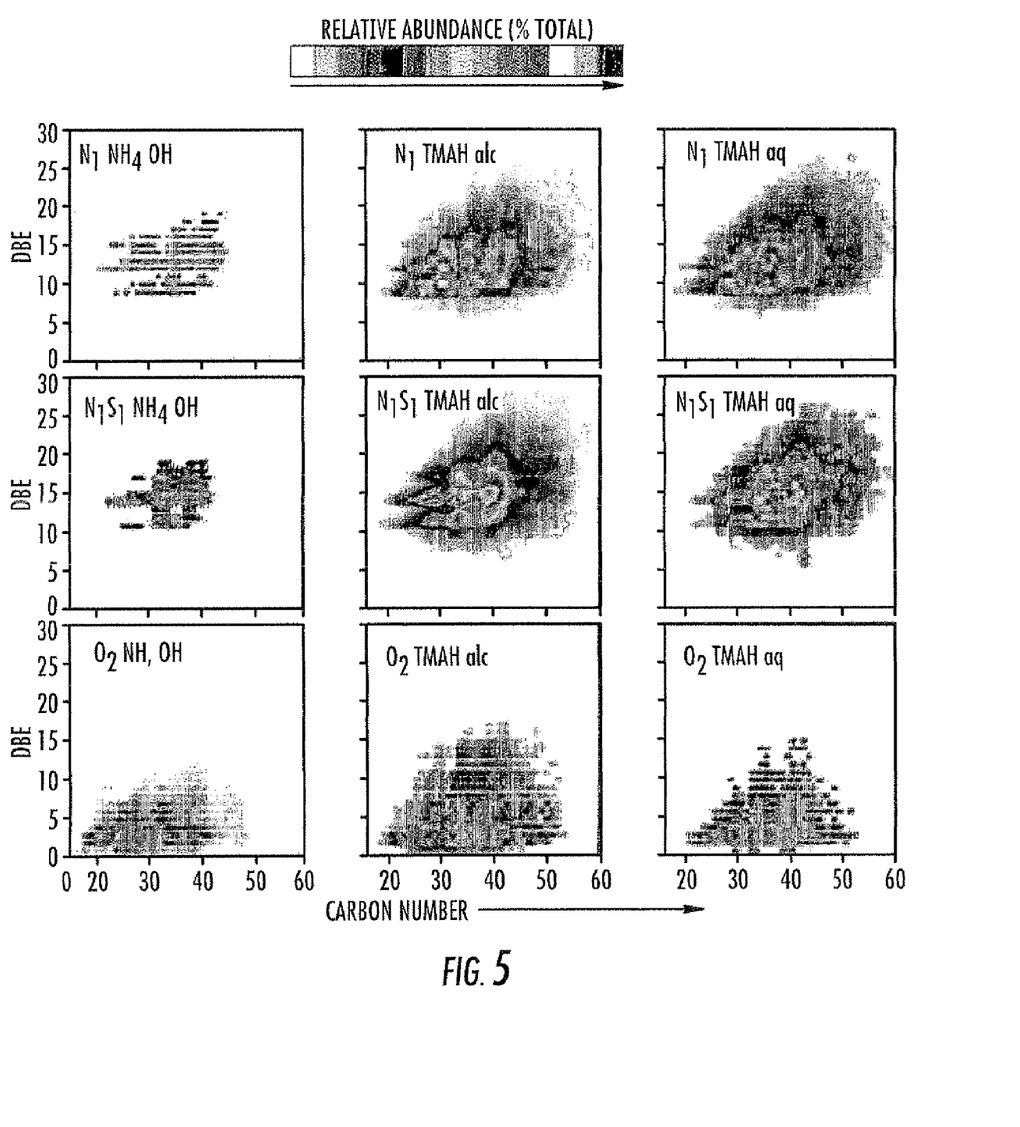
FIG. 5 is a series of graphs of negative ion mode ESI FT-ICR MS results showing the isoabundance-contoured DBE versus carbon number images for $N_1$, $N_1S_1$ and $O_2$ classes for a Canadian bitumen sample obtained using ammonium hydroxide, organic TMAH, and aqueous TMAH.

FIG. 5 demonstrates that the ionization of the $N_1$ class is greatly increased by TMAH addition compared to samples tested using ammonium hydroxide. Specifically, the classes with two or more oxygens, e.g., carboxylic acids, and sulfur oxy-acids show a disproportionately higher relative abundance with ammonium hydroxide. In contrast, classes with one oxygen and the nitrogen class, possibly phenols and pyrroles, exhibit higher relative abundance with TMAH. It is believed that this effect can be ascribed to the ability of TMAH to extract a proton from relatively weak acids, so that the molecular classes that were insufficiently ionized with ammonium hydroxide are efficiently deprotonated and accurately detected. Thus, TMAH provides improved speciation of numerous classes of heteroatom compounds found in crude oils and bitumen.

FIG. 5 shows that ESI MS using TMAH also generates hydrocarbon (HC) class ions that have never been observed as negative ions using ammonium hydroxide. In addition, sulfur classes $S_1$ and $S_2$, possibly thiophenols, are also detected with TMAH, but not with ammonium hydroxide. Clearly, these TMAH results reveal enhanced compositional coverage even for the $O_2$ although it is 8-fold lower in abundance relative to the conventional ammonium hydroxide.

Figure 6:
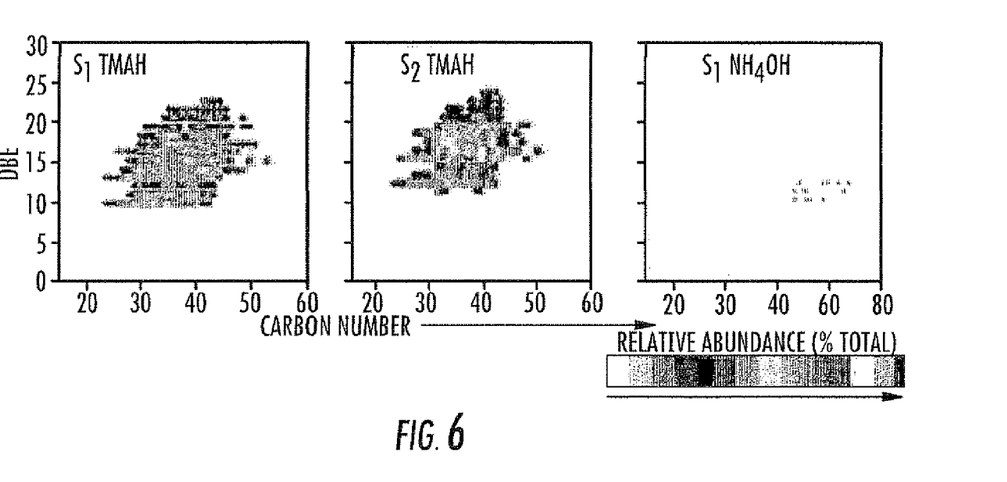
FIG. 6 is a series of graphs of negative ion mode ESI FT-ICR MS results showing the isoabundance-contoured DBE versus carbon number images for $S_1$ and $S_2$ classes for a Canadian bitumen sample using TMAH and ammonium hydroxide.

This is demonstrated by FIG. 6 in which Canadian bitumen samples tested using TMAH clearly detect $S_1$ and $S_2$ classes over a DBE from 10 to 25 and a carbon number from 20 to 50. In contrast, the same Canadian bitumen samples tested using ammonium hydroxide do not provide any useful information regarding $S_1$ or $S_2$ class compounds.

This data clearly demonstrates that using compounds of Formula I, e.g., tetramethyl ammonium hydroxide, as the ionization reagent for negative ion mode ESI FT-ICR MS is extremely effective at generating comprehensive speciation profiles of crude oil acids over a wide DBE and carbon number range. Compounds of Formula I, including TMAH, allow for the efficient ionization and subsequent detection of stable species in much lower concentration in the sample matrix and more accurately represent the relative abundances of different acidic compound classes. In contrast, ammonium hydroxide over-emphasizes the carboxylic acids and sulfur oxy-acids.

EXAMPLE 2

Samples and Sample Preparation

Three different crude oil samples, Light Sour, San Joaquin Valley (SJV) and Cerro Negro, were utilized to determine the differences in speciation between ammonium hydroxide and tetramethylammonium hydroxide on the detection of acidic crude oil species. The ESI FT-ICR mass spectrometer system described in Example 1 was used for analysis.

Methanol and toluene of HPLC grade, TMAH (25% in methanol) and ammonium hydroxide (28% of $NH_3$ in water) were used in the highest commercially available purity and were procured from Fisher-Scientific. All of the crude oil samples were dissolved in a 1:1 (v/v) solution of toluene/methanol. TMAH and ammonium hydroxide were spiked at a concentration of 10 μL per mL of sample. The reagents and sample solutions were vortexed for a few seconds before the spray. Optimal conditions for the generation of ions for petroleum samples by ESI were used. A fused-silica micro ESI needle with a 50 μm inner diameter (ID) was used to deliver each sample to the ionization source via a syringe pump at a rate of 400 nL/min under typical ESI conditions (2.1 kV; tube lens, 350 V and heated metal capillary operated at ~10 W).

Results and Discussion

For data presentation, graphs showing color-coded iso-abundant contours representing double bond equivalents (DBE, the number of rings plus double bonds) versus carbon number distributions for selected class as used. These plots allow interpretation a substantial amount of spectral information in a compact form. FIGS. 7-12 show a comparison of heteroatom class distribution obtained for each of the three crude oils using negative ion ESI with ammonium hydroxide and tetramethylammonium hydroxide. From these graphs, it is evident that the speciation of compound classes substantially improves with the use of TMAH compared with ammonium hydroxide. It appears that this is a result of significant changes in the basicity of the solvent system.

Figure 7:
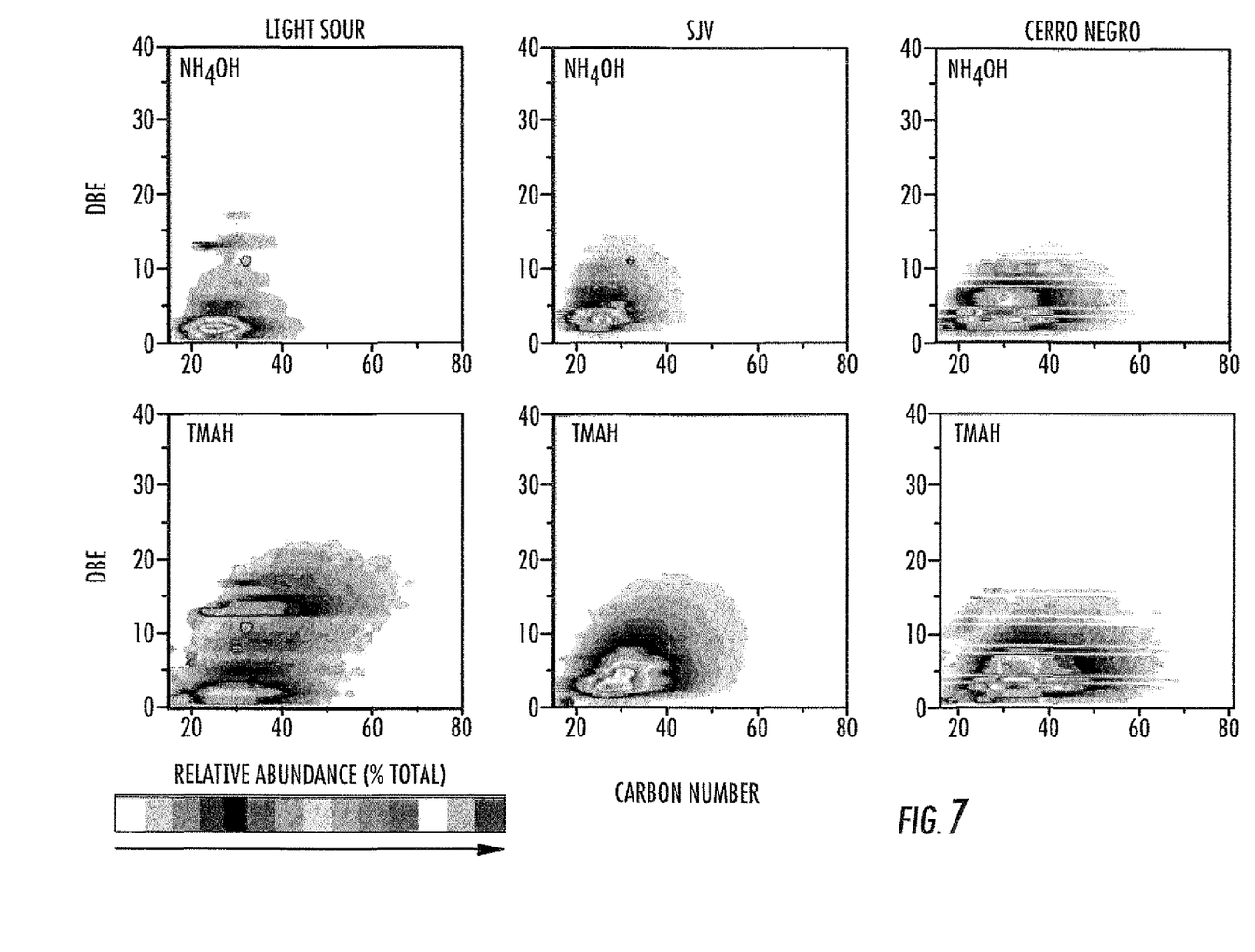
FIG. 7 is a series of graphs of negative ion mode ESI FT-ICR MS results showing the isoabundance-contoured DBE versus carbon number images for $O_2$ classes for Light Sour, San Joaquin Valley (SJV) and Cerro Negro oil samples using TMAH and ammonium hydroxide.

FIG. 7 demonstrates difference in $O_2$ class (carboxylic acids) distribution obtained with $NH_4OH$ and TMAH. For all crudes the DBE versus carbon number plots show wider range (higher values of DBE and carbon number) and increased relative abundance of carboxylic acids detected in TMAH spiked samples. However, the mass spectra of Cerro Negro crude oil (characterized by high TAN value correlating to a high content of carboxylic acids) obtained with $NH_4OH$ and TMAH demonstrate comparable relative abundance but wider range for the $O_2$ species detected in the case of TMAH. Thus, TMAH reveals enhanced compositional coverage for all three oil types—Light Sour, San Joaquin Valley (SJV) and Cerro Negro.

Figure 8:
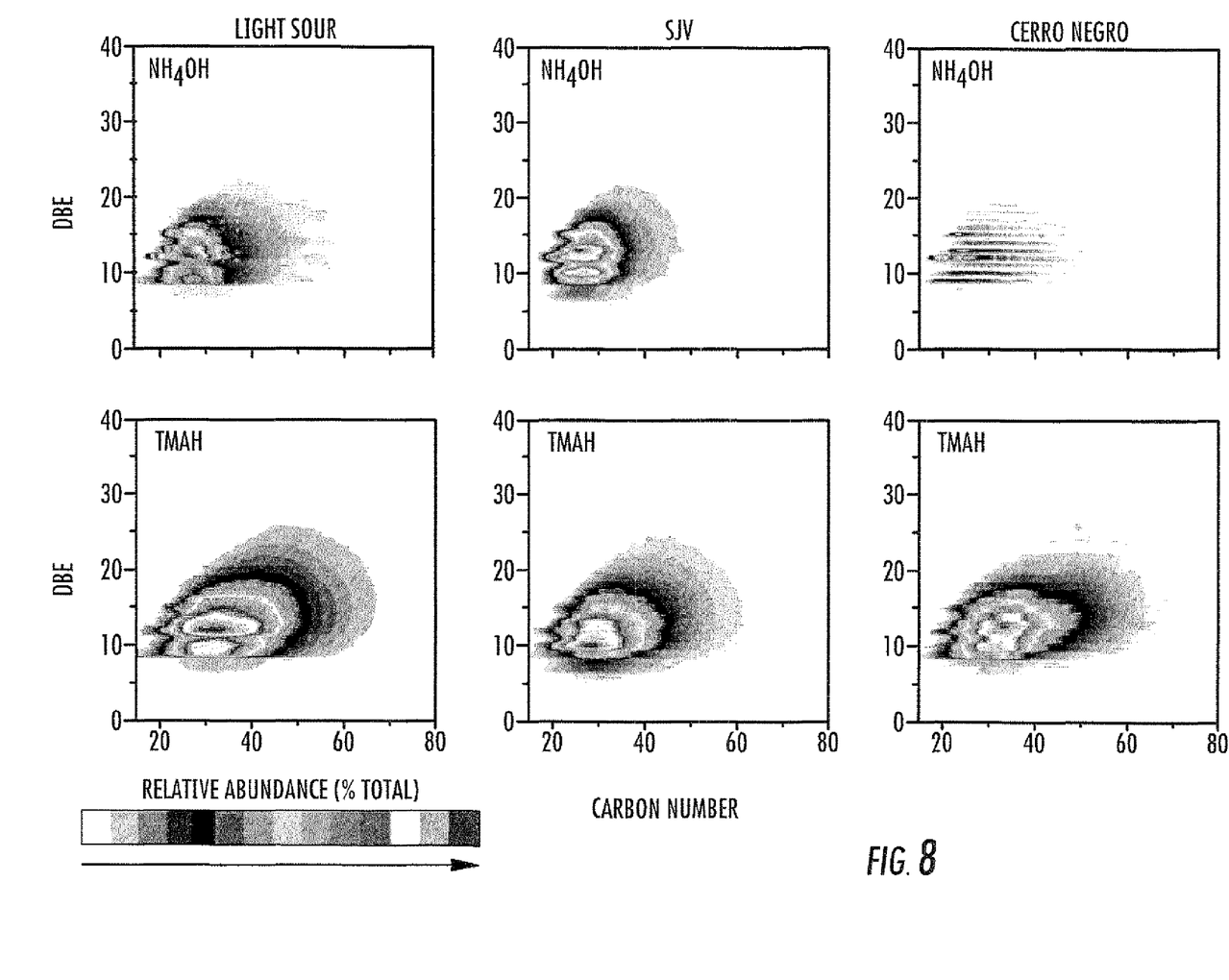
FIG. 8 is a series of graphs of negative ion mode ESI FT-ICR MS results showing the isoabundance-contoured DBE versus carbon number images for $N_1$ classes for Light Sour, San Joaquin Valley (SJV) and Cerro Negro oil samples using TMAH and ammonium hydroxide.

The difference in performance of $NH_4OH$ and TMAH is even more distinct in the case of less acidic $N_1$ class. FIG. 8 shows a comparison of DBE versus carbon number distribution for all three oils for heteroatom class $N_1$ derived from the two different reagents. Compounds belonging to $N_1$ class have the most abundant peaks in the mass spectra of TMAH spiked samples. The plots display TMAH produces a broader distribution of $N_1$ species with a carbon distribution $15<C<70$, and a DBE distribution of $6<DBE<26$ shown in FIG. 8. It is likely that $N_1$ class corresponds to pyrrol/indole/carbazole type molecules and the increase in relative abundance with TMAH can be ascribed to the ability of TMAH to withdraw a proton from the relatively weak acids, e.g., pyrrol with a $pK_a$ of approximately 23, indole with a $pK_a$ of approximately 21), and carbazole with a $pK_a$ of approximately 19.9

Figure 9:
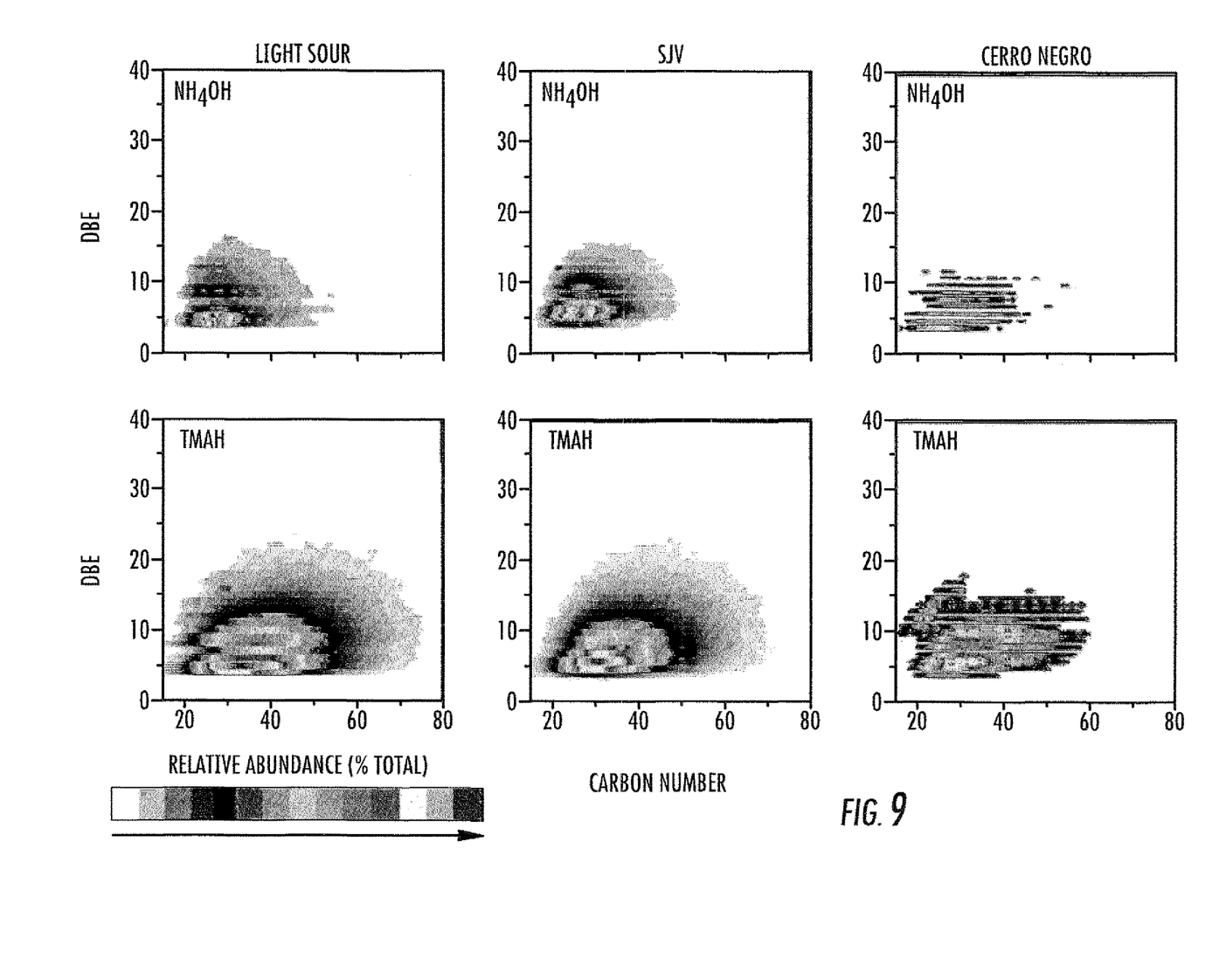
FIG. 9 is a series of graphs of negative ion mode ESI FT-ICR MS results showing the isoabundance-contoured DBE versus carbon number images for $O_1$ classes for Light Sour, San Joaquin Valley (SJV) and Cerro Negro oil samples using TMAH and ammonium hydroxide.

As shown in FIG. 9, the DBE vs. Carbon number contours make it clear that TMAH is better at ionization of the $O_1$ class, which are weak acids over a higher DBE and carbon number values. The compounds of the $O_1$ class are likely to belong to phenols that are week acids and are ionized with a stronger base such as TMAH more efficiently.

Figure 10:
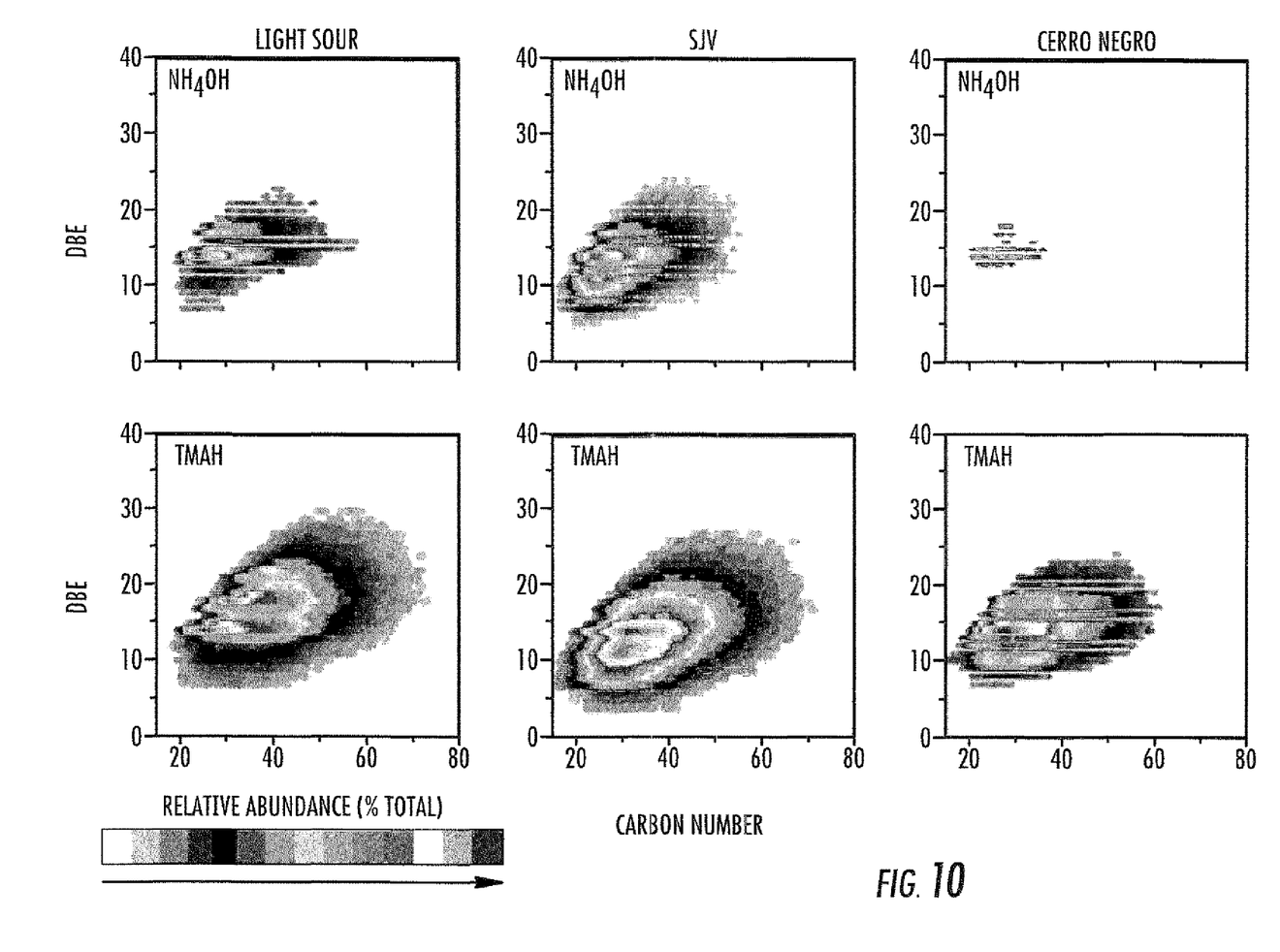
FIG. 10 is a series of graphs of negative ion mode ESI FT-ICR MS results showing the isoabundance-contoured DBE versus carbon number images for $N_1O_1$ classes for Light Sour, San Joaquin Valley (SJV) and Cerro Negro oil samples using TMAH and ammonium hydroxide.
Figure 11:
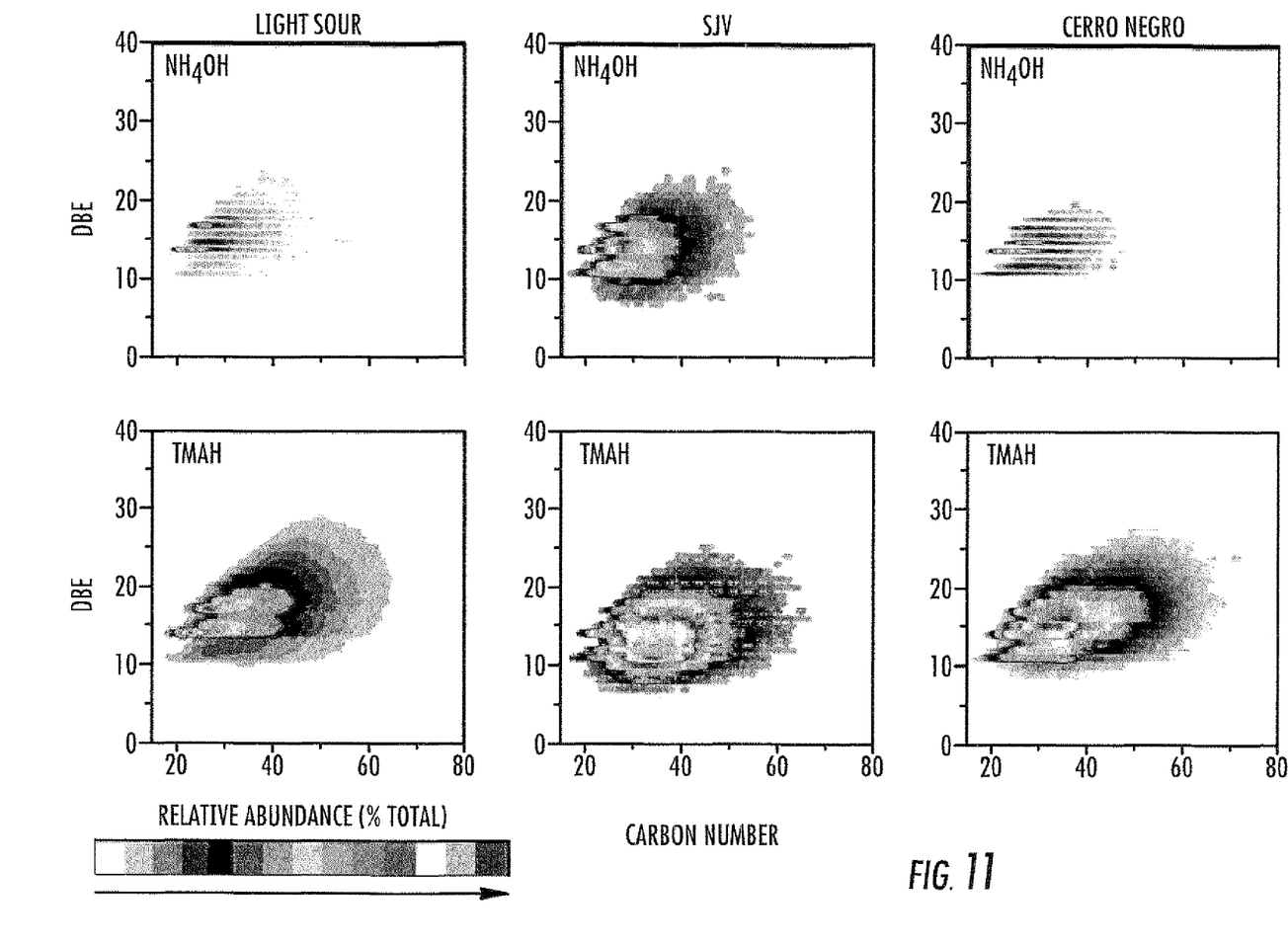
FIG. 11 is a series of graphs of negative ion mode ESI FT-ICR MS results showing the isoabundance-contoured DBE versus carbon number images for $N_1S_1$ classes for Light Sour, San Joaquin Valley (SJV) and Cerro Negro oil samples using TMAH and ammonium hydroxide.

FIGS. 10 and 11 also demonstrate the superiority of TMAH over ammonium hydroxide as a reagent for deprotonation of $N_1O_1$ and $N_1S_1$ classes, respectively. Images obtained with TMAH extend to higher values of DBE and carbon numbers. FIG. 10 shows that $N_1O_1$ class for Cerro Negro crude oil is hardly visible with $NH_4OH$ while it is well observed in the case of TMAH. Similarly, FIG. 11 shows that TMAH is superior to ammonium hydroxide for detection of $N_1S_1$ classes for Light Sour and Cerro Negro crude oils. Thus, these less acidic classes can be easily under-estimated or completely omitted at the use of $NH_4OH$.

Figure 12:
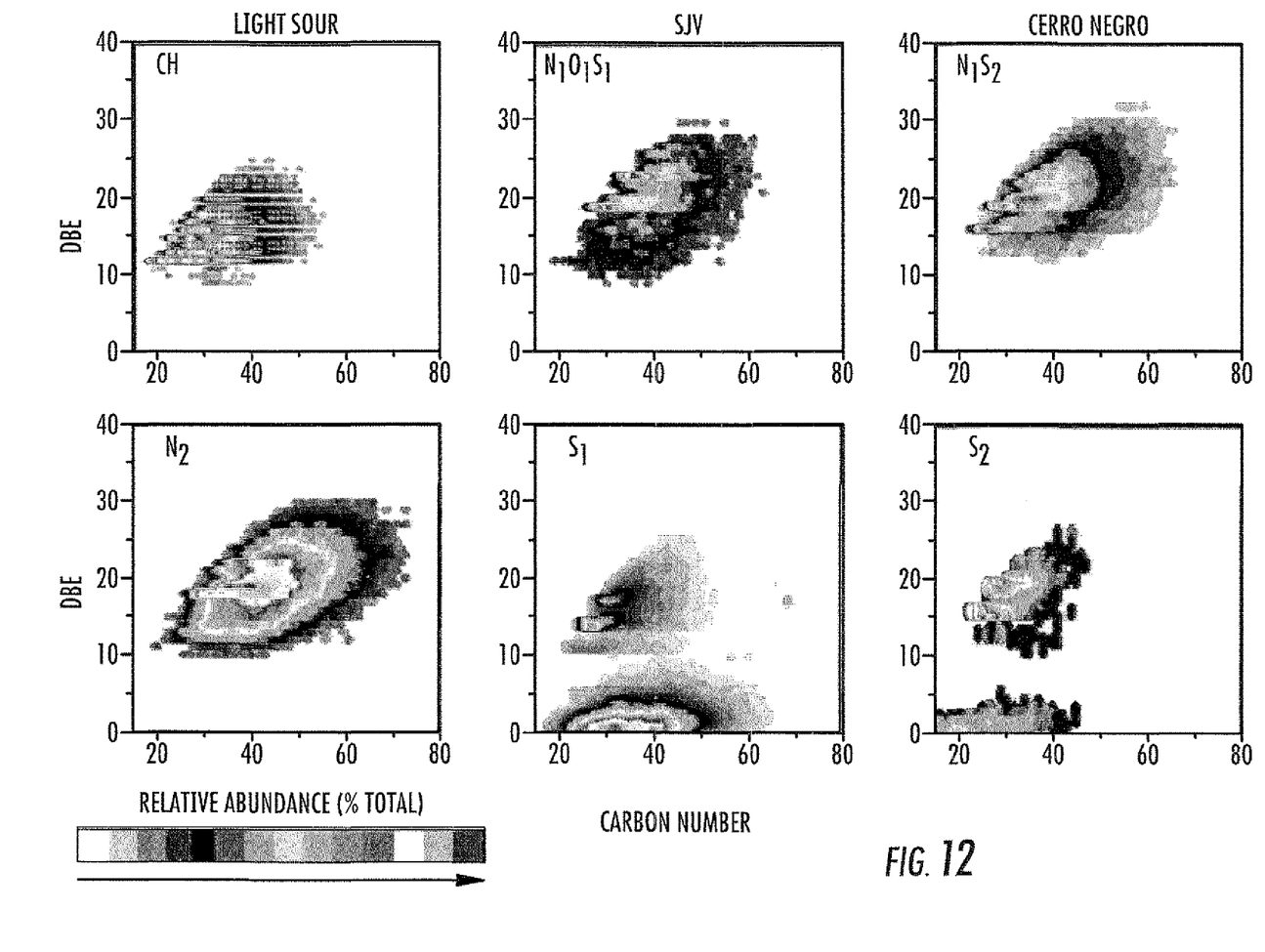
FIG. 12 is a series of graphs of negative ion mode ESI FT-ICR MS results showing the isoabundance-contoured DBE versus carbon number images for CH, NOS, $NS_2$, $N_2$, $S_1$ and $S_2$ for Light Sour oil samples using TMAH.

FIG. 12 includes plots for CH, NOS, $N_1S_2$, $N_2$, $S_1$ and $S_2$ classes obtained for Light Sour crude oil with TMAH. The signal for these classes is either absent (CH, NOS, $NS_2$, $S_2$ classes) or very week ($N_2$, $S_1$ classes) at the use of $NH_4OH$. Thus, TMAH provides significantly improved information and is suitable for detection of classes with a higher heteroatom content. Hydrocarbon class (CH) appears at a DBE of 9-24, which indicate condensed polycyclic structures. A lower DBE observed is 9 and is likely to correspond to fluorenyl anion (alkyl) derivatives. As discussed above such cyclic compounds can be deprotonated from the $sp^3$ carbon in the presence of an extremely strong base to generate resonance-stabilized carbanions. NOS, $N_1S_2$, $N_2$ classes are detected in the wide range of DBE (from 9 to over 30) and Carbon number (from 20 to 70) and appear to have either pyrolic nitrogen (NOS, $N_1S_2$, $N_2$ classes), or/and thio-group (NOS, $N_1$ $S_2$ classes) or/and phenolic group (NOS class). $S_1$ and $S_2$ classes contain two region of information. The low DBE region (DBE 0-3) suggests thiols while the high DBE of 10 to 25 implies the presence of thiophenoles (deprotonation of —SH group) or/and condensed polycyclic sulfur-containing compounds deprotonating through the mechanism similar to that for CH class (deprotonation of sp$^3$-hybridized carbon next to aromatic core).

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A method of enhanced speciation of an analyte, the method comprising:
   obtaining an analyte composition;
   producing a first analyte solution comprising said analyte composition and an effective amount of silver triflate;
   analyzing said first analyte solution with an electrospray ionization mass spectrometer;
   producing a second analyte solution comprising a portion of said analyte composition and an effective amount of a compound of formula I; and
   analyzing said second analyte solution with an electrospray ionization mass spectrometer, wherein said compound of formula I is:
   [NX$_4^+$][OH$^-$], where X is a linear, branched, or cyclic C$_1$-C$_{10}$ alkane; an aryl; a heterocyclic aromatic; or a heterocyclic moiety.

2. The method of enhanced speciation of an analyte of claim 1, wherein said compound of formula I is tetrabutylammonium hydroxide or tetramethyl ammonium hydroxide.

3. The method of enhanced speciation of an analyte of claim 1, wherein said compound of formula I is tetramethyl ammonium hydroxide.

4. The method of enhanced speciation of an analyte of claim 1, wherein said analyte composition comprises a nonpolar compound.

5. The method of enhanced speciation of an analyte of claim 1, wherein said analyte composition comprises crude oil, bitumen, a fraction thereof, a concentrate thereof, or a component thereof.

6. The method of enhanced speciation of an analyte of claim 1, wherein said analyzing of said first analyte solution comprises analyzing said first analyte solution with said electrospray ionization mass spectrometer in positive ion mode.

7. The method of enhanced speciation of an analyte of claim 1, wherein said analyzing of said second analyte solution comprises analyzing said second analyte solution with said electrospray ionization mass spectrometer in negative ion mode.

8. The method of enhanced speciation of an analyte of claim 1, wherein said analyzing of said first analyte solution comprises analyzing said first analyte solution with said electrospray ionization mass spectrometer in positive ion mode, and said analyzing of said second analyte solution comprises analyzing said second analyte solution with said electrospray ionization mass spectrometer in negative ion mode.

9. An electrospray ionization mass spectrometry methodology, comprising:
   obtaining an analyte solution comprising an analyte composition and an effective amount of a compound of formula I; and
   analyzing said analyte solution with an electrospray ionization mass spectrometer, wherein said compound of formula I is:
   [NX$_4^+$][OH$^-$], where X is a linear, branched, or cyclic C$_1$-C$_{10}$ alkane; an aryl; a heterocyclic aromatic; or a heterocyclic moiety.

10. The electrospray ionization spectrometry methodology of claim 9, wherein said compound of formula I is tetrabutylammonium hydroxide or tetramethyl ammonium hydroxide.

11. The electrospray ionization spectrometry methodology of claim 9, wherein said compound of formula I is tetramethyl ammonium hydroxide.

12. The electrospray ionization spectrometry methodology of claim 9, wherein said analyte composition comprises a petroleum compound.

13. The electrospray ionization spectrometry methodology of claim 9, wherein said analyte composition comprises crude oil, bitumen, a fraction thereof, a concentrate thereof, or a component thereof.

14. The electrospray ionization spectrometry methodology of claim 9, wherein said analyzing step comprises analyzing said analyte solution with said electrospray ionization mass spectrometer in negative ion mode.

15. The electrospray ionization spectrometry methodology of claim 9, wherein a mass ratio of analyte composition to compound of Formula I ranges from 10,000:1 to 1:3.

16. An electrospray ionization mass spectrometry methodology, comprising:
   obtaining an analyte solution comprising an analyte composition and an effective amount of silver triflate; and
   analyzing said analyte solution with an electrospray ionization mass spectrometer.

17. The electrospray ionization spectrometry methodology of claim 16, wherein said analyte composition comprises a petroleum compound.

18. The electrospray ionization spectrometry methodology of claim 16, wherein said analyte composition comprises crude oil, bitumen, a fraction thereof, a concentrate thereof, or a component thereof.

19. The electrospray ionization spectrometry methodology of claim 16, wherein said analyzing step comprises analyzing said analyte solution with said electrospray ionization mass spectrometer in positive ion mode.

20. The electrospray ionization spectrometry methodology of claim 16, wherein a mass ratio of analyte composition to silver triflate ranges from 3:1 to 1:10.

* * * * *